US012350172B2

(12) United States Patent
Kleyman et al.

(10) Patent No.: US 12,350,172 B2
(45) Date of Patent: Jul. 8, 2025

(54) SYSTEMS AND METHODS FOR TRAINING AND USING AN IMPLANT PLAN EVALUATION MODEL

(71) Applicant: Mazor Robotics Ltd., Caesarea (IL)

(72) Inventors: Leonid Kleyman, Atzmon Misgav (IL); Liron Itan, Hadera (IL); Noa Mor, Tel Aviv (IL); Anna Ostap Yaacoby, Haifa (IL); Or Riven, Haifa (IL); Adi Steinmetz, Tel Aviv (IL); Dor Artzi, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 903 days.

(21) Appl. No.: 17/203,187

(22) Filed: Mar. 16, 2021

(65) Prior Publication Data

US 2022/0296388 A1  Sep. 22, 2022

(51) Int. Cl.
*A61F 2/46* (2006.01)
*A61B 34/00* (2016.01)
*A61B 34/20* (2016.01)
*A61B 34/30* (2016.01)
*A61F 2/44* (2006.01)
*G06N 20/00* (2019.01)
*G16H 20/40* (2018.01)
*G16H 50/50* (2018.01)

(52) U.S. Cl.
CPC .......... *A61F 2/46* (2013.01); *A61F 2/44* (2013.01); *G06N 20/00* (2019.01); *G16H 20/40* (2018.01); *G16H 50/50* (2018.01); *A61B 34/20* (2016.02); *A61B 2034/252* (2016.02); *A61B 34/30* (2016.02); *A61F 2002/4633* (2013.01)

(58) Field of Classification Search
CPC ...... A61F 2/46; A61F 2/44; A61F 2002/4633; G16H 20/40; G16H 50/50; G06N 20/00; A61B 34/20; A61B 2034/252; A61B 34/30
See application file for complete search history.

(56) References Cited

U.S. PATENT DOCUMENTS

| 2009/0162813 A1* | 6/2009 | Glor ....................... A61C 1/084 433/196 |
| 2010/0191071 A1* | 7/2010 | Anderson ............... G16H 50/50 703/11 |
| 2010/0191100 A1* | 7/2010 | Anderson ................ G06T 7/246 600/424 |

(Continued)

*Primary Examiner* — Kevin T Truong
*Assistant Examiner* — Diana Jones
(74) *Attorney, Agent, or Firm* — Sheridan Ross P.C.

(57) ABSTRACT

Systems and methods for training an implant plan evaluation model is provided. A first implant plan option having a first set of parameters and a second implant plan option having a second set of parameters may be received. The first set of parameters and the second set of parameters may be inputted into a model configured to score the first implant plan option based on the first set of parameters and the second implant plan option based on the second set of parameters. The score of the first implant plan option and the score of the second implant plan option may be compared. when the score of the second implant plan option is higher than the score of the first implant plan option the model may be adjusted to score the first implant plan option higher than the second implant plan option.

16 Claims, 3 Drawing Sheets

(56) References Cited

U.S. PATENT DOCUMENTS

2010/0256504 A1* 10/2010 Moreau-Gaudry .... A61B 34/20
                                                  703/11
2019/0146458 A1    5/2019  Roh et al.
2020/0188026 A1*  6/2020  de Souza .............. G06T 7/0016
2020/0315708 A1   10/2020  Mosnier et al.

* cited by examiner

SYSTEMS AND METHODS FOR TRAINING AND USING AN IMPLANT PLAN EVALUATION MODEL

FIELD

The present technology generally relates to surgical planning, and relates more particularly to automatically training and using an implant plan evaluation model for planning the placement and parameters of one or more implants.

BACKGROUND

Planning one or more surgical steps for a surgical plan is based on several factors and inputs. Surgeons may identify one or more implants to insert during a surgical procedure based on one or more of the factors and inputs. Surgical robots may assist a surgeon or other medical provider in carrying out the one or more surgical procedures, or may complete the one or more surgical procedures autonomously.

SUMMARY

Example aspects of the present disclosure include:

A method for training an implant plan evaluation model according to at least one embodiment of the present disclosure comprises receiving, at a processor, a first implant plan option having a first set of parameters and a second implant plan option having a second set of parameters, the first implant plan option generated with user input; inputting, with the processor, the first set of parameters and the second set of parameters into a model configured to score the first implant plan option based on the first set of parameters and the second implant plan option based on the second set of parameters; comparing, using the processor, the score of the first implant plan option and the score of the second implant plan option; and when the score of the second implant plan option is higher than the score of the first implant plan option, adjusting the model to score the first implant plan option higher than the second implant plan option.

Any of the aspects herein, further comprising: inputting to the model, with the processor, parameters corresponding to each implant plan option of a set of implant plan options, to yield a score for each implant plan option; and selecting, using the processor, the implant plan option, from the set of implant plan options, with the highest score.

Any of the aspects herein, further comprising: displaying, using the processor, the selected implant plan option on a user interface.

Any of the aspects herein, further comprising: generating, using the processor, a surgical step for a surgical plan based on the selected implant plan option.

Any of the aspects herein, further comprising: prompting a user to accept the selected implant plan option.

Any of the aspects herein, wherein at least one of the first set of parameters or the second set of parameters comprises a surgical parameter or a safety parameter.

Any of the aspects herein, wherein the first implant plan option is defined by a user and the second implant plan option is generated automatically.

Any of the aspects herein, further comprising: receiving, by the processor, at least one image; determining, using the processor, at least one constraint based on the at least one image; and generating, automatically using the processor, a set of implant plan options based on the at least one constraint.

Any of the aspects herein, wherein the adjusting the model to score the first implant plan option higher than the second implant plan option comprises determining a weight for at least one parameter of the first set of parameters and the second set of parameters.

Any of the aspects herein, wherein each of the first implant plan option and the second implant plan option corresponds to placement options for a spinal implant.

A method for training an implant plan evaluation model according to at least one embodiment of the present disclosure comprises receiving, by a processor, a plurality of constraints; determining, using the processor, a set of implant plan options that meet the plurality of constraints; scoring each of the set of implant plan options using a model trained with training data comprising pairs of implant plan options, each pair comprising a first implant plan option defined by user input and a second implant plan option generated automatically; and selecting, using the processor, the implant plan option with the highest score.

Any of the aspects herein, wherein the model was trained at least in part by comparing a score assigned by the model to the first implant plan option and to the second implant plan option and, when the score of the second implant plan option was higher than the score of the first implant plan option, adjusting the model to score the first implant plan option higher than the second implant plan option.

Any of the aspects herein, wherein receiving the plurality of constrains comprises: receiving, at the processor, at least one image; and determining, using the processor, the plurality of constraints based on the at least one image.

Any of the aspects herein, further comprising: displaying, using the processor, the selected implant plan option on a user interface.

Any of the aspects herein, further comprising: generating, using the processor, a surgical step for a surgical plan based on the selected implant plan option.

Any of the aspects herein, wherein at least one of the set of implant plan options comprises a surgical parameter or a safety parameter.

Any of the aspects herein, wherein the first implant plan option is defined by a user and the second implant plan option is generated automatically.

Any of the aspects herein, wherein the adjusting the model to score the first implant plan option higher than the second implant plan option comprises determining a weight for at least one parameter of the set of implant plan options.

A method/system for training a model according to at least one embodiment of the present disclosure comprises at least one user interface; at least one processor; and at least one memory storing instructions for execution by the at least one processor that, when executed, cause the at least one processor to: receive a first implant plan option having a first set of parameters and a second implant plan option having a second set of parameters; input the first set of parameters and the second set of parameters into a model configured to score the first implant plan option based on the first set of parameters and the second implant plan option based on the second set of parameters; compare the score of the first implant plan option and the score of the second implant plan option; and when the score of the second implant plan option is higher than the score of the first implant plan option, adjust the model to score the first implant plan option higher than the second implant plan option.

Any of the aspects herein, wherein the memory stores additional instructions for execution by the at least one processor that, when executed, further cause the at least one processor to: input to the model, parameters corresponding to each implant plan option of a set of implant plan options to yield a score for each implant plan option; select the implant plan option from the set of implant plan options with the highest score; and display the selected implant plan option on the at least one user interface.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
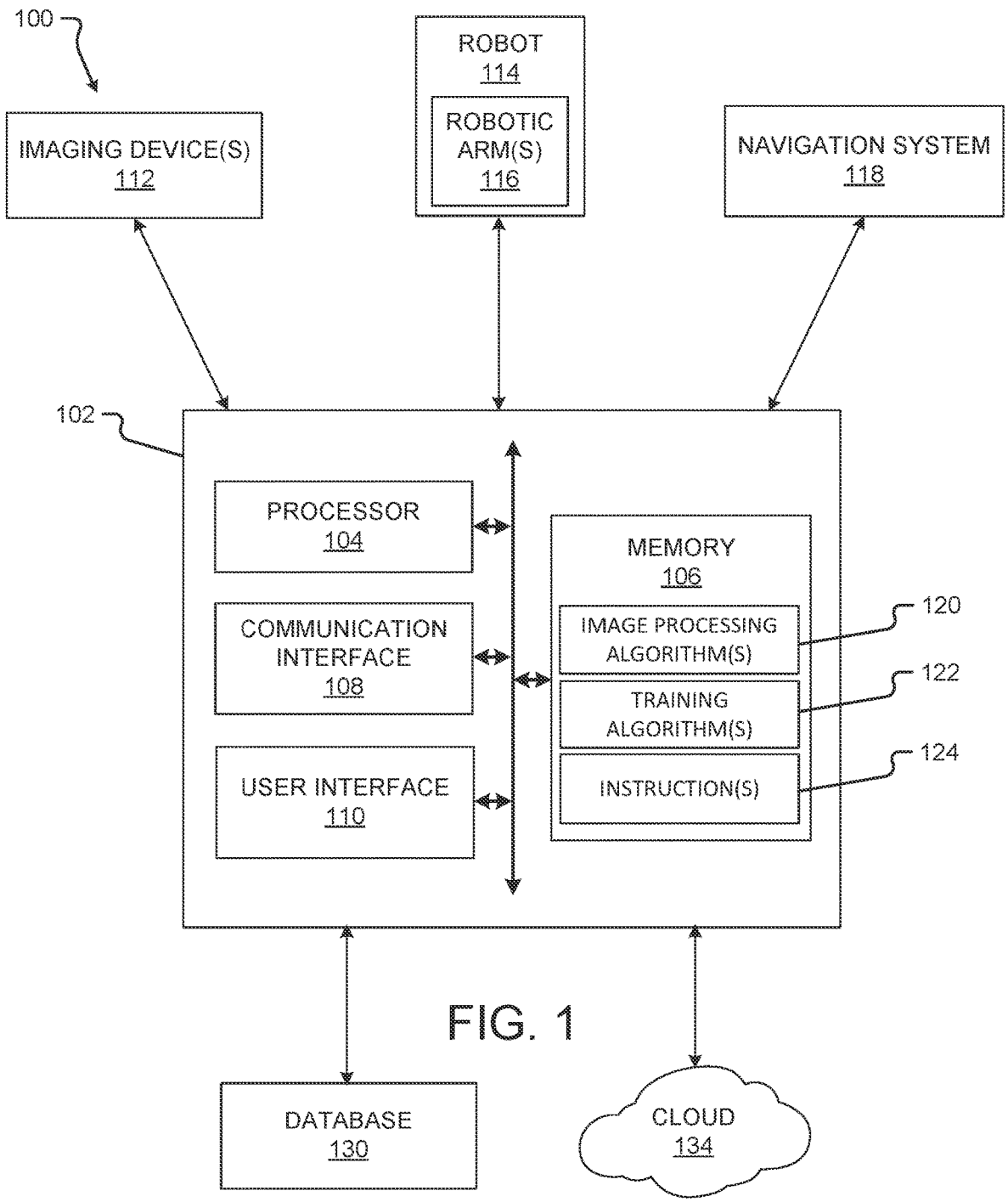
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Embodiments of the present disclosure are useful for automatically planning a pose and one or more parameters of implants, such as screws, used in spine surgery and placed inside one or more vertebrae on which the surgery is performed. In some spine surgery procedures, an exterior rod construct may pass through holes located at an end of each screw to assist in fixing the set of vertebrae in a desired posture.

The pose and the one or more parameters of the screws planned for the surgery may be determined based on a set of clinical constraints. First, the screws need to be securely attached to the one or more vertebrae and to withstand the load and forces exerted on them. This may be addressed by making the screws as long and as wide as possible. Second, constraints arising from the operation itself are considered. For example, the orientation of each screw may be selected to match the planned incision to minimize the pressure on the screw. Further, an axial angle and an elevation angle of the screw may be small enough such that a width of the incision may be minimized, and an entry angle may be selected to alleviate the danger of the drill slipping (e.g., skiving) during the surgery. While these constraints can be measured and valued mathematically, the solutions may not converge to a singular solution. As such, the methods and systems according to embodiments of the present disclosure generate screw or other implant plans that reflect the screw or other implant plans made by experts. This is accomplished by combining learnings from examples generated by one or more experts with physical and clinical constraints arising from and/or specific to the surgery itself.

There may be several valid screw options when planning to implant a set of screws, with each screw option characterized by one or more different parameters. An importance of each parameter for a given screw or set of screws may not be clearly established and thus, there may be considerable variation among surgeons as to which of multiple screw options is preferred.

Embodiments of the present disclose may apply a score to the possible screw options for the surgery. According to at least one embodiment of the present disclosure, a score for a particular screw option is calculated as follows: First, a large set of screw options that meet constraints as determined clinically by the surgery is calculated. Then, a score for each screw option is defined, with the score representing a "probability" of an expert choosing that particular option with its particular parameters. Machine learning may be used to train a model that determines the score (e.g., "probability") for each screw option. The model is trained using a dataset consisting of pairs of two screw options, one of which is a screw option generated and/or selected by a human expert, and the second of which is a different option from the large data set of screws options. The model performs the same grade calculation for both screw options, giving a "probability" score for each one. The scores of both options are then compared and, if necessary, the model is updated to give a higher "probability" to the human expert screw option, in comparison with the other non-human screw option.

When using the trained model for proposing a screw, the trained model is used on each option in the screw options set (e.g., the set of screw options that all meet the clinical constraints of the surgery). Then the screw option with the highest score—which is the screw option with the highest "probability" of being chosen by an expert—is selected. In some embodiments, the "probability" or score is the output of the net or other model which increases a monotonic function corresponding to the probability of an expert selecting the screw option. Although the foregoing description is provided in the context of vertebral screws, embodiments of the present disclosure may be used to plan the parameters and/or pose of any implant having multiple parameter and/or pose options.

Embodiments of the present disclosure provide technical solutions to one or more of the problems of (1) automatically planning the placement and parameters of one or more implants (including by generating placement and parameter options and selecting one set of placement and parameter options), (2) automatically selecting one or more implants, (3) training an implant plan evaluation model, (4) using an implant plan evaluation model, and/or (5) improving selection of one or more implants.

Turning first to FIG. 1, a block diagram of a system 100 according to at least one embodiment of the present disclosure is shown. The system 100 may be used to train and/or use an implant plan evaluation model for automatically selecting and/or determining a planned pose and/or parameter(s) of an implant. The system 100 may also be used to carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200 and/or 300 described herein, or of any other methods. The memory 106 may store, for example, one or more image processing algorithms 120, one or more training algorithms 122, and/or instructions 124. Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computing device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The system 100 or similar systems may be used, for example, to carry out one or more aspects of any of the methods 200 and/or 300 described herein. The system 100 or similar systems may also be used for other purposes.

Figure 2:
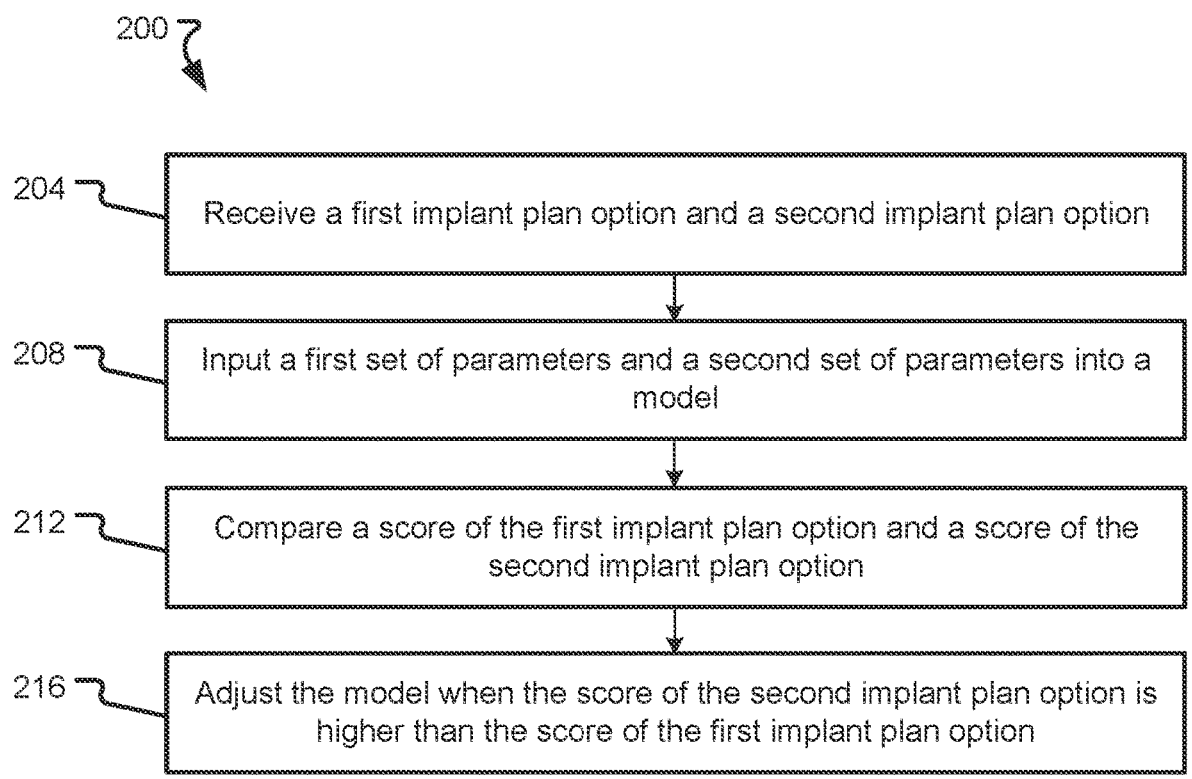
FIG. 2 is a flowchart according to at least one embodiment of the present disclosure.

FIG. 2 depicts a method 200 that may be used, for example, for training an implant plan evaluation model. The implant plan evaluation model may be trained using, for example, a training algorithm such as the training algorithm 122.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as an image processing algorithm 120, a training algorithm 122, and/or instructions 124.

The method 200 comprises receiving a first implant plan option and a second implant plan option (step 204). The first implant plan option and the second implant plan option may be received via a user interface such as the user interface 110 and/or a communication interface such as the communication interface 108 of a computing device such as the computing device 102, and may be stored in a memory such as the memory 106 of the computing device. The first implant plan option and the second implant plan option may also be received from an external database (e.g., a health information system (HIS), and/or another system for collecting, storing, managing, and/or transmitting electronic medical records), and/or via the Internet or another network. In some embodiments, the first implant plan option and the second implant plan option may be indirectly received via any other component of a system such as the system 100 or a node of a network to which the system is connected.

Each of the first implant plan option and the second implant plan option correspond to placement options and/or parameters for a spinal implant. It will be appreciated that an implant plan option (whether a first implant plan option, a second implant plan option, or any implant plan option) may include an implant to be used, a pose for the implant, and/or any other relevant information. The first implant plan option may be generated with user input (e.g., by a user). For example, a surgeon or other medical provider may manually design the first implant plan option. "Designing" the first implant plan option may comprise selecting an implant (and/or specifying one or more implant parameters) and/or specifying a pose at which the implant will be implanted. In another example, the surgeon or other medical provider may use a planning software to design the first implant plan option. The second implant plan option may be generated automatically. The second implant plan option may be generated by any component of a system such as the system 100. For example, the second implant plan option may be generated by a processor such as the processor 104. Generating the second implant plan option may be based on a plurality of constraints, which may be based on surgical constraints during a surgical procedure and/or anatomical constraints of a patient.

The first implant plan option may include a first set of parameters and the second implant plan option may include a second set of parameters. As noted above, the first set of parameters may be specified by a surgeon or other expert, whether indirectly (e.g., by selecting an implant having the parameters) or directly (e.g., by specifying the parameters themselves). Similarly, the second set of parameters may be determined automatically, whether based on surgical constraints associated with a surgical procedure or otherwise. The first set of parameters and/or the second set of parameters may comprise, for example, one or more surgical parameters and/or one or more safety parameters. The one or more surgical parameters may be one or more of, for example, a screw diameter, a screw elevation angle in relation to a vertebra orientation, a screw entry angle into a vertebra, a screw length, a screw axial angle in relation to the vertebra orientation, a measurement of a curvature of a surface of an anatomical element, how closely a calculated entry surface matches an actual anatomical surface around the entry point, and/or a standard deviation of a distance from a surface (actual and/or calculated) to a screw. The safety parameter may be one or more of, for example, a distance between a tip of a screw and a center of a cylindrical volume of a pedicle in which a screw can be inserted, a distance between a center of a cylindrical volume of a pedicle in which a screw can be inserted and a screw in a X-direction, a distance between a center of a cylindrical volume of a pedicle in which a screw can be inserted and a screw in a Y-direction, a distance between a pedicle center of mass and a screw in an X-direction, a distance between a pedicle center of mass and a screw in a Y-direction, a difference between a direction vector of a cylindrical volume of a pedicle in which a screw can be inserted and a direction vector of a screw on an X-axis, and/or a difference between a direction vector of a cylindrical volume of a pedicle in which a screw can be inserted and a direction vector of a screw on a Y-axis. The screw entry angle is calculated relative to the entry surface, which in turn is calculated using a set of points around the entry point. Accordingly, one or more parameters may correspond to how closely the calculated entry surface matches or approximates the actual anatomical surface surrounding the entry point.

The method 200 also comprises inputting the first set of parameters and the second set of parameters into a model (step 208). The model may be configured to score the first implant plan option based on the first set of parameters and the second implant plan option based on the second set of parameters. The scoring may comprise inputting the first set of parameters and the second set of parameters (and/or one or more subsets thereof) into one or more algorithms. The algorithms may be configured, for example, to weight the parameters received as inputs. Where more than one algorithm is used for the scoring, the results of each algorithm may be combined (e.g., using addition, subtraction, multiplication, division, and/or any other mathematical operations) in a predetermined way.

The resulting score may correlate to a predicted probability that a surgeon or a medical provider will select the first implant plan option or the second implant plan option for a surgical procedure. In some embodiments, the score constitutes a ranking that corresponds to a likelihood that an expert (such as a surgeon or other medical provider) would select the implant option in question relative to the other considered implant options. Alternatively, the score for each implant option may correlate to an estimated probability (whether absolute or relative) of an expert (such as a surgeon or other medical provider) selecting the particular implant option for a planned surgical procedure.

The resulting score is a relative score (as opposed to an absolute score such as a go/no-go score). In some embodiments, the scoring of the first implant plan option and the second implant plan option is scored using any numerical scale (e.g., 1-10, 1-20, etc.). In other embodiments, the first implant plan option and the second implant plan option are scored using any other scale (such as color, likelihood, graphical, etc.). In some embodiments, the model simply outputs which of the two implant plan options is more likely to be selected by a surgeon or other medical provider.

The step 208 may also comprise extracting the first set of parameters and/or the second set of parameters from information about the first implant plan option and/or the second implant plan option. In some embodiments, the parameters may be separately listed and easily inputted, but in others, an extraction process may be used to determine the parameters for inputting into the model.

The method 200 also comprises comparing a score of the first implant plan option and a score of the second implant plan option (step 212). The comparing may also include calculating a difference in the score of the first implant plan option and the score of the second implant plan option. The purpose of the comparing is to identify which of the two implant plan options is more likely, as reflected by the score thereof, to be selected by a surgeon or other healthcare provider.

The method 200 also comprises adjusting the model when the score of the second implant plan option is higher than the score of the first implant plan option (step 216). The adjusting may be automatically executed by the processor. For example, machine learning or other artificial intelligence (which may include or use, for example, a training algorithm 122) may be used to analyze the first and second sets of parameters and make one or more changes to the model that would result in the first implant plan option scoring higher than the second implant plan option. In other embodiments, the adjusting may be manually performed by, for example, a surgeon or other medical provider. The adjusting updates the model to score the first implant plan option higher than the second implant plan option. In some embodiments, the adjusting step may comprise adjusting the model when the difference (calculated in step 212, for example) between the scores of the first implant plan option and the second implant plan option is greater than a predetermined threshold.

The step 216 may also comprise determining or updating a weight for at least one parameter of the first set of parameters and/or the second set of parameters. Such determination of weight(s) may be used to affect the impact of a given parameter on a score of an implant plan option, which may correlate to whether a parameter is important to an expert. In other words, a parameter with a higher weight may be a parameter that an expert would consider more important than other parameters. For example, in open surgery an axial angle may not be as important as other parameters and thus, may be assigned a lower weight than other parameters. In other examples, a length of a screw may be more important than other parameters, and thus, may be assigned a higher weight than other parameters. Determination of a proper weight for each parameter may be accomplished manually (e.g., without the assistance of a processor such as the processor 104), with computer assistance, and/or fully autonomously. Machine learning or other artificial intelligence may be used to identify parameters of importance to a surgeon or other expert (e.g., in the context of a given set of surgical constraints) and/or to determine a weight to assign a given parameter.

By adjusting the score of the first implant plan option (which is generated by an expert such as a surgeon or other medical provider, as described above) to be higher than the score of the second implant plan option (which may be automatically generated), the model is trained to automatically select an implant from a set of implants that an expert (such as a surgeon or other medical provider) is more likely to select. In other words, the model is trained to consider and favor preferences of an expert (such as a surgeon or other medical provider)—as inferred by machine learning or other artificial intelligence, by comparing expert-created implant plan options to implant plan options created automatically or otherwise—in selecting an implant.

The method 200 is used to train a model to identify, from among a plurality of implant plan options, an implant plan option that is most likely to be selected by an expert. Such training may involve repeatedly iterating the method 200, each time with different implant plan options (one generated or otherwise selected by a surgeon or other expert and another generated automatically or otherwise) and associated parameter sets, and/or with a different set of surgical constraints. Such training may be considered to be complete when, for example, the model correctly identifies (e.g., by assigning a better score to) the implant plan option generated by the expert.

The present disclosure encompasses embodiments of the method 200 that comprise more or fewer steps than those described above, and/or one or more steps that are different than the steps described above.

Figure 3:
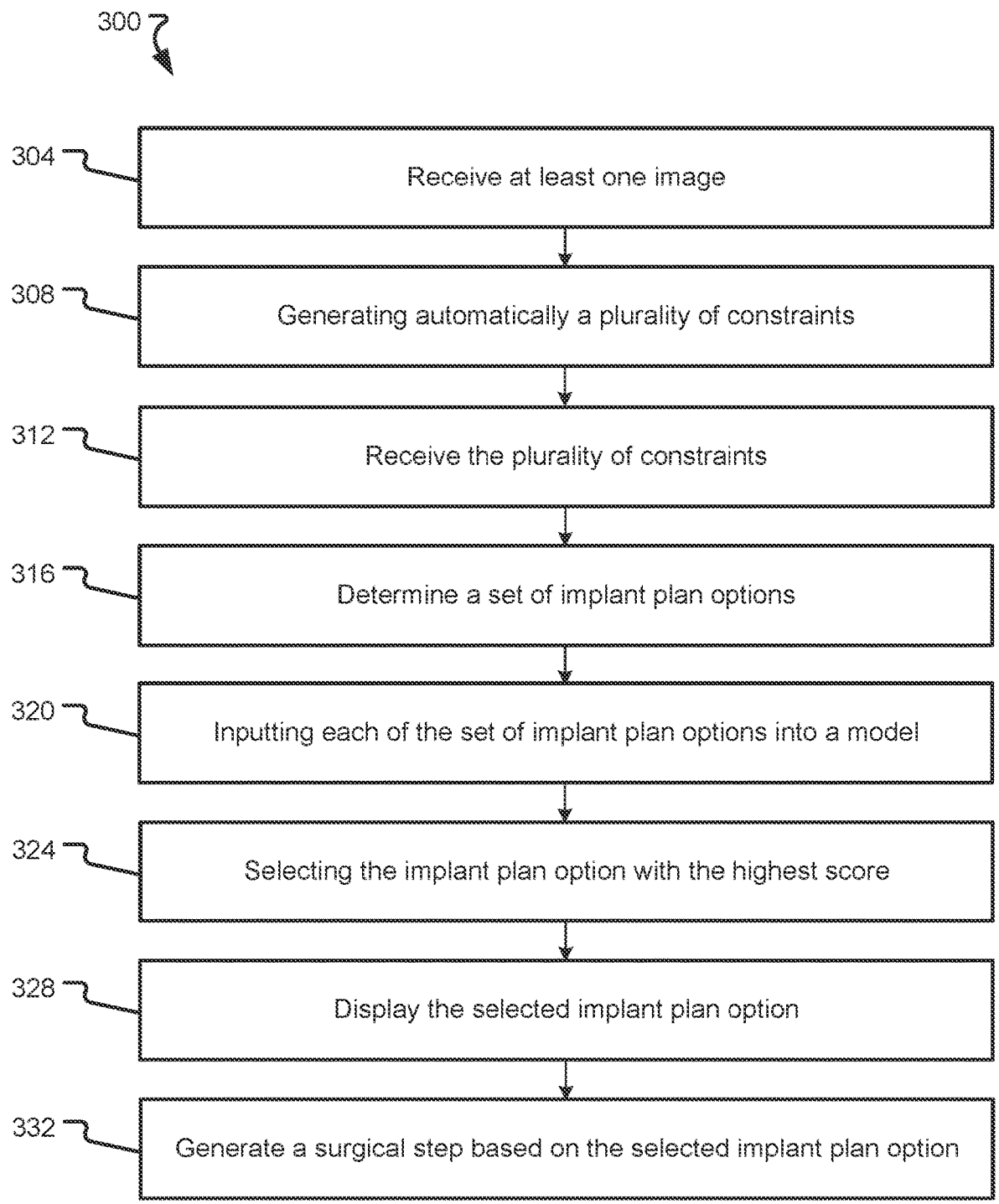
FIG. 3 is a flowchart according to at least one embodiment of the present disclosure.

FIG. 3 depicts a method 300 of using an implant plan evaluation model. By using the implant plan evaluation model, a pose and at least one parameter of one or more implants may be automatically planned. In some embodiments, the implants may be a set of screws and the surgical procedure may be a spinal procedure.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as an image processing algorithm 120, a training algorithm 122, and/or instructions 124.

The method 300 comprises receiving at least one image (step 304). The image may be received via a user interface such as the user interface 110 and/or a communication interface such as the communication interface 108 of a computing device such as the computing device 102, and may be stored in a memory such as the memory 106 of the computing device. The image may also be received from an external database or image repository (e.g., a hospital image storage system, such as a picture archiving and communication system (PACS), a health information system (HIS), and/or another system for collecting, storing, managing, and/or transmitting electronic medical records including image data), and/or via the Internet or another network. In other embodiments, the image may be received or obtained from an imaging device such as the imaging device 112, which may be any imaging device such as an MRI scanner, a CT scanner, any other X-ray based imaging device, or an ultrasound imaging device. The image may also be generated by and/or uploaded to any other component of a system such as the system 100. In some embodiments, the image may be indirectly received via any other component of the system or a node of a network to which the system is connected.

The image may comprise one or more 2D images, one or more 3D images, a 3D model, or a combination of one or more 2D images and one or more 3D images. In some embodiments, one imaging device may be used to obtain the image. In other embodiments, multiple imaging devices may be used to obtain the image. In examples wherein more than one image is received or multiple images are used to construct a 3D image, a first imaging device may obtain a first one of the images independently of a second imaging device obtaining a second one of the images. In another example, at least a first one of the images may be obtained with a first imaging device and at least a second one of the images may be obtained with a second imaging device.

The image may be processed using an image processing algorithm such as the image processing algorithm 120 to identify one or more features in the image. In some embodiments, feature recognition (using, e.g., an edge detection or other feature recognition algorithm) may be used to identify a feature of an anatomical element, a tool, and/or an instrument. For example, a contour of a vertebra, femur, or other bone may be identified in the image. In other embodiments, segmentation may be used to identify an anatomical element in the image.

The method 300 also comprises automatically generating a plurality of constraints (step 308). In some embodiments, the generating may be based on the at least one image received in step 304. For example, a constraint may be an angle of insertion of a screw into a pedicle (relative, e.g., to a plane tangent to the surface of the pedicle at the point of insertion). Such constraint may be determined from measuring the angle of insertion in the at least one image (wherein the at least one image depicts at least one vertebra). Another constraint may be, for example, a maximum length of a screw, which may be determined by a dimension of the at least one vertebra, which in turn may also be measured in the at least one image). In other embodiments, the constraints may be based on a surgical procedure to be performed. For example, an orientation of an implant trajectory may be determined based at least in part on a planned incision in a surgical plan. The plurality of constraints ensures that an implant (e.g., a screw) is appropriate for the anatomy involved, is securely attached to an anatomical element (e.g., a vertebra) and can withstand the load and forces expected to be exerted onto the implant.

The method 300 also comprises receiving the plurality of constraints (step 312). When the plurality of constraints are generated in the step 308 described above, the step 312 may (in some embodiments) be omitted from the method 300. Similarly, when the plurality of constraints are received as described in connection with this step 312, the steps 304 and/or 308 may (in some embodiments) be omitted from the method 300. Alternatively, in some embodiments, the plurality of constraints may be generated via steps 304 and 308 by a first processor, for example, of a first computing device, and the generated plurality of constraints may be received via step 312 by a second processor, for example, of a second computing device.

The plurality of constraints may be received via a user interface such as the user interface 110 and/or a communication interface such as the communication interface 108 of a computing device such as the computing device 102, and may be stored in a memory such as the memory 106 of the computing device. The plurality of constraints may also be received from an external database (e.g., a hospital image storage system, such as a health information system (HIS), and/or another system for collecting, storing, managing, and/or transmitting electronic medical records including image data), and/or via the Internet or another network. In some embodiments, the plurality of constraints may be indirectly received via any other component of a system such as the system 100 or a node of a network to which the system is connected.

The method 300 also comprises determining a set of implant plan options (step 316). The set of implant plan options may be determined based on the plurality of constraints generated in step 308 and/or received in step 312. In such determinations, each implant plan option of the set of implant plan options may meet each of the plurality of constraints. In some embodiments, the set of implant plan options may be generated or calculated automatically by, for example, a processor such as the processor 104. In other embodiments, the set of implant plan options may be generated or calculated by a human (e.g., a surgical technician, a surgeon or other medical provider).

The method 300 also comprises inputting parameters corresponding to each implant plan option of the set of implant plan options into a model (step 320). The parameters may comprise one or more surgical parameters and/or one or more safety parameters. The one or more surgical parameters may be or include one or more of, for example, a screw diameter, a screw elevation angle in relation to a vertebra orientation, a screw entry angle into a vertebra, a screw length, a screw axial angle in relation to the vertebra orientation, a measurement of a curvature of a surface of an anatomical element, how closely a calculated entry surface matches an actual anatomical surface around the entry point, and/or a standard deviation of a distance from a surface (actual and/or calculated) to a screw. The one or more safety parameters may be or include one or more of, for example, a distance between a tip of a screw and a center of a cylindrical volume of a pedicle in which a screw can be inserted, a distance between a center of a cylindrical volume of a pedicle in which a screw can be inserted and a screw in a X-direction, a distance between a center of a cylindrical volume of a pedicle in which a screw can be inserted and a screw in a Y-direction, a distance between a pedicle center of mass and a screw in an X-direction, a distance between a pedicle center of mass and a screw in a Y-direction, a difference between a direction vector of a cylindrical volume of a pedicle in which a screw can be inserted and a direction vector of a screw on an X-axis, and/or a difference between a direction vector of a cylindrical volume of a pedicle in which a screw can be inserted and a direction vector of a screw on a Y-axis. The screw entry angle is calculated relative to the entry surface, which in turn is calculated using a set of points around the entry point. Accordingly, one or more parameters may correspond to how closely the calculated entry surface matches or approximates the actual anatomical surface surrounding the entry point.

The model may be configured to score each implant plan option of the set of implant plan options. As previously described, in some embodiments, the score constitutes a ranking that corresponds to a likelihood that an expert (such as a surgeon or other medical provider) would select the implant plan option in question relative to the other considered implant plan options. Alternatively, the score for each implant plan option may correlate to an estimated probability (whether absolute or relative) of an expert (such as a surgeon or other medical provider) selecting the particular implant plan option for a planned surgical procedure. In some embodiments, each implant plan option is scored using any numerical scale (e.g., 1-10, 1-20, etc.). In other embodiments, each implant plan option is scored using any other scale (such as color, intensity, etc.). In some embodiments, the model may simply output one or more implant plan options that is more likely to be selected by a surgeon or other medical provider.

In some embodiments, the model may be trained (prior to being used for the step 320) with training data. The training data may comprise pairs of implant plan options. Each pair may comprise a first implant plan option defined by user input and a second implant plan option generated automatically. In other embodiments, the model is trained using the steps 204-216 of method 200 described above.

The method 300 also comprises selecting the implant plan option with the highest score (step 324). The selecting may be automatically executed by a processor such as the processor 104. In other embodiments, the selecting may be manually performed by, for example, a surgeon or other medical provider. In embodiments where the selecting may be performed by a surgeon or other medical provider, the set of implant plan options and each of their corresponding scores may be displayed on a user interface such as the user interface 110. In such embodiments, the set of implant plan options may be displayed in the order of the highest scores. In other embodiments, a number of implant plan options within a range of scores may be displayed. In other embodiments, only a top number of implant plan options may be displayed. For example, the displaying may display the implant plan options with the top three highest scores and may prompt the surgeon or other medical provider to select one of the implant plan options or allow for the selection of one of the implant plan options. It will be appreciated that any number of implant plan options may be displayed in any form.

The implant plan option with the highest score may correlate to the implant plan option with the highest estimated probability that an expert (such as a surgeon or other medical provider) will choose the particular implant plan option for a surgical procedure. Once a particular implant plan option has been selected, and particularly if the selected implant plan option is not the implant plan option that received the highest score from the model, machine learning and/or other artificial intelligence may be used to analyze the various implant plan options (including the selected option and other options) and to adjust the model (as described above in connection with the step 216, for example) accordingly.

The method 300 also comprises displaying the selected implant plan option (step 328). The selected implant plan option may be displayed on a user interface such as the user interface 110. The selected implant plan option may be displayed to a surgeon or other medical provider. Displaying the selected implant plan option may also prompt the surgeon or other medical provider to accept the selected implant plan option. In some embodiments, a surgeon or other user may modify the displayed implant plan option, and then select the modified displayed implant plan option to use for carrying out the surgical procedure.

The method 300 also comprises generating a surgical step based on the selected implant plan option (step 332). The surgical step may comprise one or more steps necessary to implement the selected implant plan option. In some embodiments, the surgical step may be generated based on one or more corresponding parameters of the selected implant plan option. For example, the surgical step may include inserting an implant at an angle specified by the implant plan option, and/or using an implant having dimensions specified by the implant plan option. The surgical step may include instructions such as the instructions 124. The instructions may be generated in machine readable form or human readable form. The instructions may be transmitted to a robot such as the robot 114 to cause the robot to execute the surgical step. In other embodiments, the instructions may be communicated to a surgeon or other medical provider via a user interface such as the user interface 110.

The present disclosure encompasses embodiments of the method 300 that comprise more or fewer steps than those described above, and/or one or more steps that are different than the steps described above.

As noted above, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
   receiving, at a processor, a first implant plan option having a first set of parameters and a second implant plan option having a second set of parameters, the first implant plan option generated with user input;
   inputting, with the processor, the first set of parameters and the second set of parameters into a model configured to score the first implant plan option based on the first set of parameters and the second implant plan option based on the second set of parameters;
   comparing, using the processor, the score of the first implant plan option and the score of the second implant plan option;
   when the score of the second implant plan option is higher than the score of the first implant plan option, adjusting the model to score the first implant plan option higher than the second implant plan option,
   wherein the adjusting the model to score the first implant plan option higher than the second implant plan option comprises determining a weight for at least one parameter of the first set of parameters and the second set of parameters;
   inputting to the model, with the processor, parameters corresponding to each implant plan option of a set of implant plan options, to yield a score for each implant plan option;
   selecting, using the processor, the implant plan option of the set of implant plan options with the highest score;
   generating, using the processor, a surgical step for a surgical plan based on the selected implant plan option; and
   controlling a robot to perform the surgical step based on the selected implant plan option.

2. The method of claim 1, further comprising:
   displaying, using the processor, the selected implant plan option on a user interface.

3. The method of claim 2, further comprising:
   prompting a user to accept the selected implant plan option.

4. The method of claim 1, wherein at least one of the first set of parameters or the second set of parameters comprises a surgical parameter or a safety parameter.

5. The method of claim 1, wherein the first implant plan option is defined by a user and the second implant plan option is generated automatically.

6. The method of claim 1, further comprising:
   receiving, by the processor, at least one image;
   determining, using the processor, at least one constraint based on the at least one image; and
   generating, automatically using the processor, the set of implant plan options based on the at least one constraint.

7. The method of claim 1, wherein each of the first implant plan option and the second implant plan option corresponds to placement options for a spinal implant.

8. A method, comprising:
   receiving, by a processor, a plurality of constraints;
   determining, using the processor, a set of implant plan options that meet the plurality of constraints;
   scoring each of the set of implant plan options using a model trained with training data comprising pairs of implant plan options, each pair comprising a first implant plan option defined by user input and a second implant plan option generated automatically;
   selecting, using the processor, the implant plan option with the highest score;

generating, using the processor, a surgical step for a surgical plan based on the selected implant plan option; and controlling a robot to perform the surgical step based on the selected implant plan option.

9. The method of claim 8, wherein the model was trained at least in part by comparing a score assigned by the model to the first implant plan option and to the second implant plan option and, when the score of the second implant plan option was higher than the score of the first implant plan option, adjusting the model to score the first implant plan option higher than the second implant plan option.

10. The method of claim 9, wherein the adjusting the model to score the first implant plan option higher than the second implant plan option comprises determining a weight for at least one parameter of the set of implant plan options.

11. The method of claim 8, wherein receiving the plurality of constraints comprises:

receiving, at the processor, at least one image; and determining, using the processor, the plurality of constraints based on the at least one image.

12. The method of claim 8, further comprising:

displaying, using the processor, the selected implant plan option on a user interface.

13. The method of claim 8, wherein at least one of the set of implant plan options comprises a surgical parameter or a safety parameter.

14. The method of claim 8, wherein the first implant option is defined by a user.

15. A method, comprising:

receiving, at a processor, a first implant plan option having a first set of parameters and a second implant plan option having a second set of parameters, the first implant plan option generated with user input;

inputting, with the processor, the first set of parameters and the second set of parameters into a model configured to score the first implant plan option based on the first set of parameters and the second implant plan option based on the second set of parameters;

comparing, using the processor, the score of the first implant plan option and the score of the second implant plan option;

when the score of the second implant plan option is higher than the score of the first implant plan option, adjusting the model to score the first implant plan option higher than the second implant plan option;

inputting to the model, with the processor, parameters corresponding to each implant plan option of a set of implant plan options, to yield a score for each implant plan option;

selecting, using the processor, the implant plan option, from the set of implant plan options, with the highest score;

generating, using the processor, a surgical step for a surgical plan based on the selected implant option; and controlling a robot to perform the surgical step based on the selected implant plan option.

16. The method of claim 15, further comprising:

displaying, using the processor, the selected implant plan option on a user interface.

\* \* \* \* \*